(12) United States Patent
Raupp

(10) Patent No.: US 6,793,067 B1
(45) Date of Patent: Sep. 21, 2004

(54) CONTAINER INSPECTION MACHINE

(75) Inventor: Henry F. Raupp, Freeville, NY (US)

(73) Assignee: Emhart Glass S.A., Cham (CH)

( * ) Notice: Subject to any disclaimer, the term of this patent is extended or adjusted under 35 U.S.C. 154(b) by 0 days.

(21) Appl. No.: 10/610,233

(22) Filed: Jun. 30, 2003

(51) Int. Cl.[7] ............................................. B65G 15/14
(52) U.S. Cl. ............................... 198/626.5; 198/626.2; 198/606; 198/379
(58) Field of Search ................................ 1198/379, 412, 1198/604, 606, 608, 626.1, 626.2, 626.4, 626.5, 817

(56) References Cited

U.S. PATENT DOCUMENTS

| 3,901,381 A | * | 8/1975 | Quinn | 198/379 |
| 5,823,317 A | * | 10/1998 | Bankuty et al. | 198/379 |
| 6,109,426 A | * | 8/2000 | Messer, III | 198/817 |
| 6,390,282 B1 | * | 5/2002 | Ouellette | 198/626.5 |
| 6,622,851 B1 | * | 9/2003 | Wunscher | 198/626.2 |

* cited by examiner

Primary Examiner—James R. Bidwell
(74) Attorney, Agent, or Firm—Spencer T. Smith

(57) ABSTRACT

A machine for inspecting containers has a belt drive having upper and lower pairs of belt drives. Each belt drive has its own motor and each opposed pair of belt drives can be relatively horizontally displaced and as a unit displace vertically so that 1. the upper drive belt pair can be raised clear of the lower drive belt pair;
2. the lower drive belt pair can be separated and lowered to an out of the way location; and
3. the upper drive belt pair can then be lowered to be the only belt pair engaging a small container.

3 Claims, 6 Drawing Sheets

CONTAINER INSPECTION MACHINE

The present invention relates to machines which inspect bottles for defects and more particularly to such machines wherein a bottle is conveyed through one or more inspection stations via a belt conveyor having opposed pairs of belts.

BACKGROUND OF THE INVENTION

A state of the art glass bottle inspection machine wherein the bottles are transported through a number of inspection stations by a belt drive mechanism having opposed pairs of horizontal belts is disclosed in U.S. Pat. No. 5,422,476.

OBJECT OF THE INVENTION

It is an object of the present invention to provide an improved belt drive for such machines.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE PREFERRED EMBODIMENT

Figure 1:
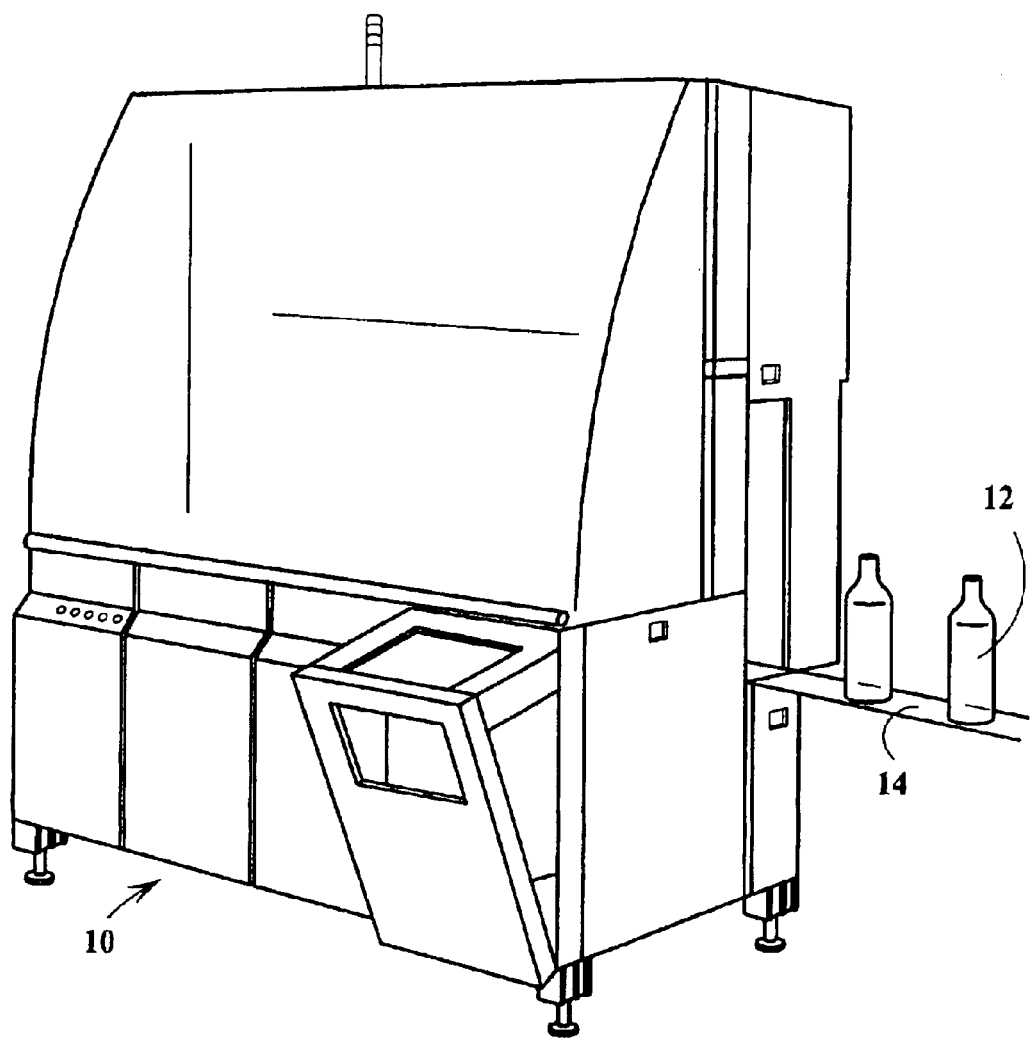
FIG. 1 is a schematic oblique view of an inspection machine for inspecting bottles made in accordance with the teachings of the present invention.

FIG. 1 is a schematic showing of an inspection machine 10 which inspects a row of bottles 12 conveyed to the machine by an infeed conveyor 14. Any of a variety of inspections can be carried out by the machine.

Figure 2:
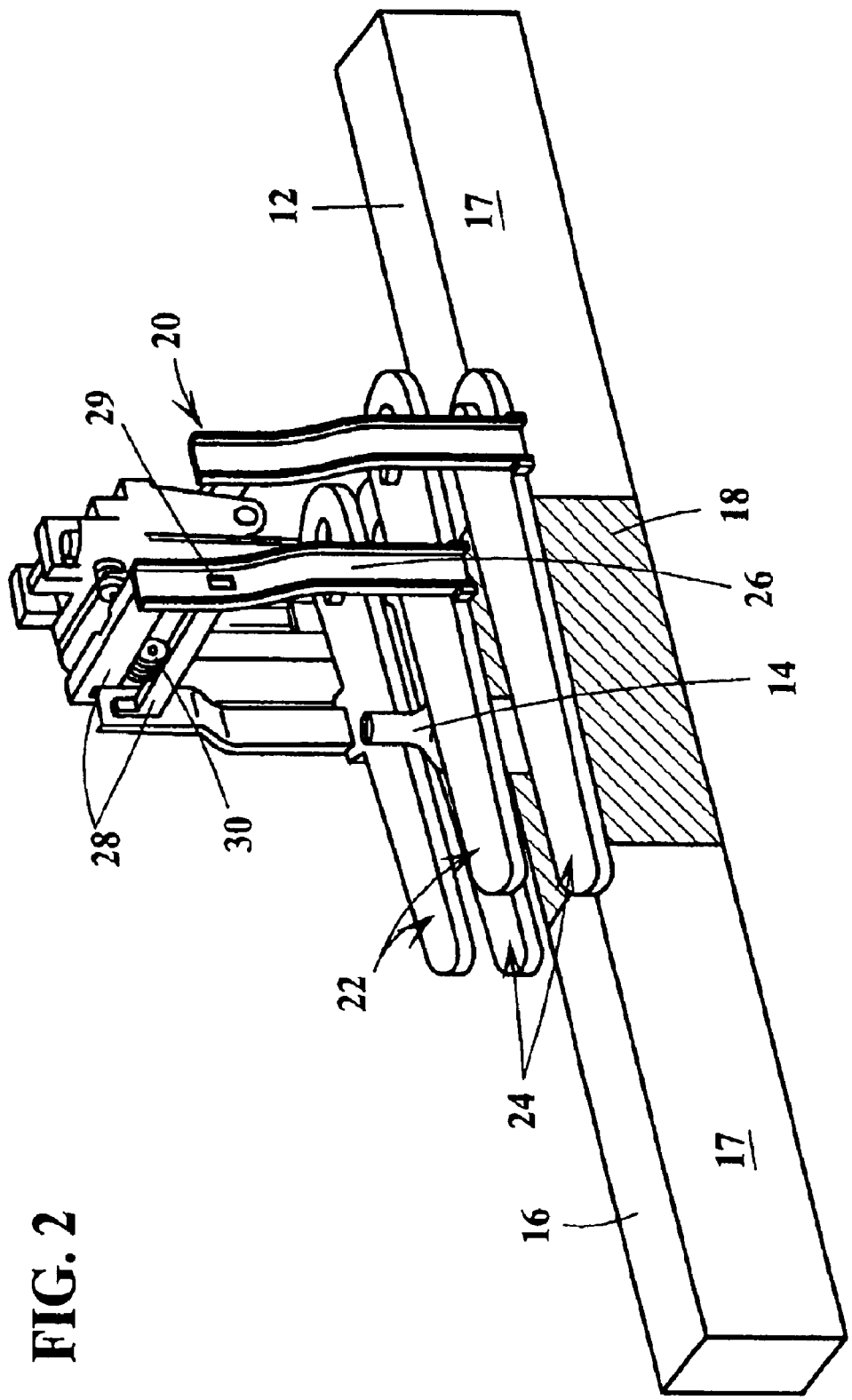
FIG. 2 is an oblique view of the belt drive assembly of the machine illustrated in FIG. 1 in the large ware configuration.

FIG. 2 illustrates the belt conveyor mechanism 20 for this machine which receives bottles from the infeed conveyor, conveys them through one or more inspection locations, and releases them to a discharge conveyor 16. The infeed and discharge conveyors have front guards 17, which, together with a front guard 18 for the inspection equipment (light sources, cameras, etc.) defines the front face of the conveyor infeed/discharge conveyor system.

As can be seen, the belt conveyor mechanism has an upper opposed pair of belt drives 22 and a lower opposed pair of belt drives 24. Each of the belt drives 22 is cantilevered from a vertical strut 26 which is integral with a horizontal slide member 28.

Figure 4:
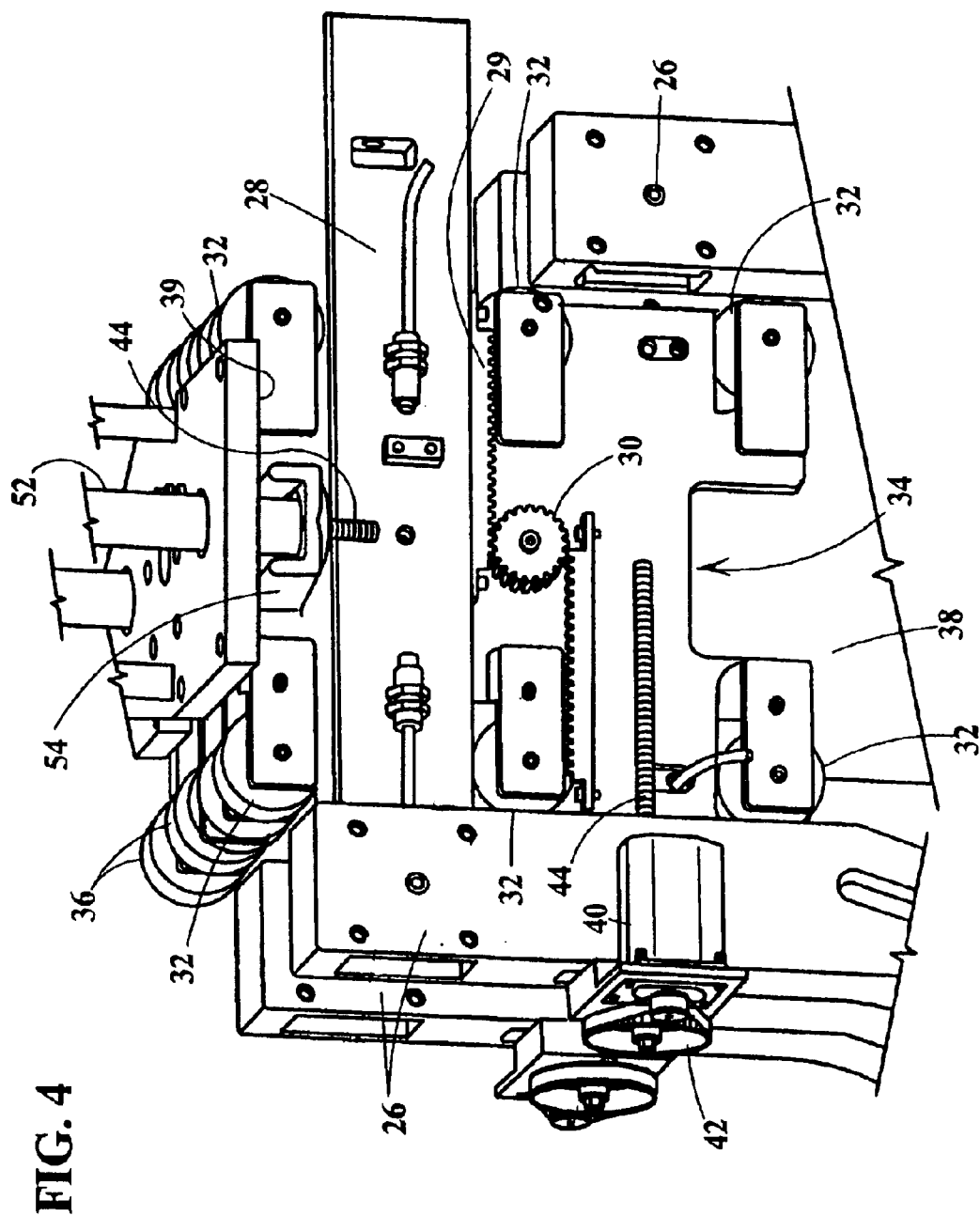
FIG. 4 is an oblique view of the belt drive assembly housing including the open/close step motors.

The two slide members of the upper/lower opposed pair of belt drives each include a rack portion 29 (one shown in FIG. 4) which is operatively associated with a drive pinion 30.

Figure 3:
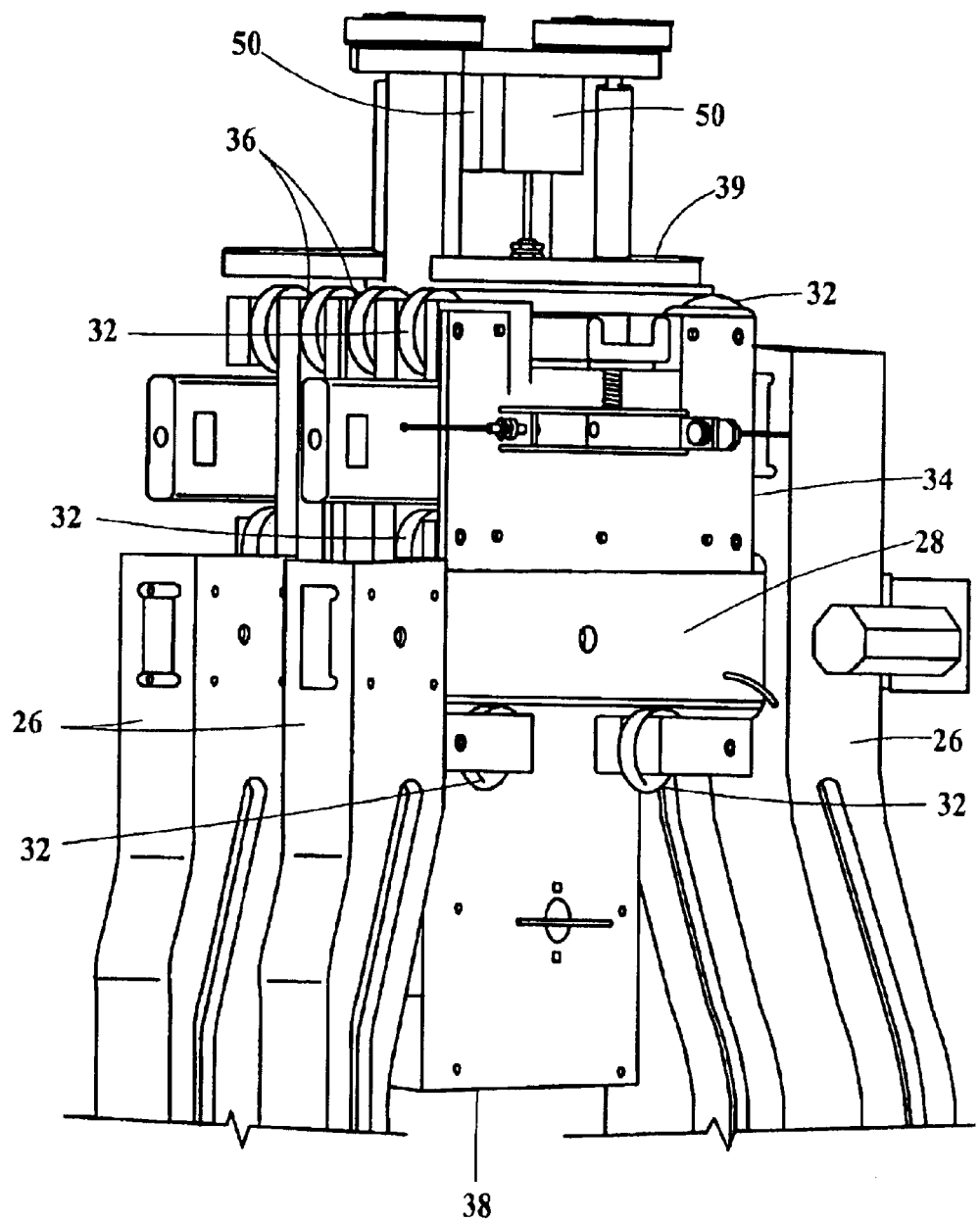
FIG. 3 is an oblique view of a guide wheel assembly for one of the opposed belt drives.

The two slide members of an opposed pair of belt drives are supported for lateral displacement by three pairs of rollers 32 (FIGS. 3 and 4) which are mounted on a carriage 34. The top slide member is supported between the top and middle roller pair and the bottom slide member is supported between the middle and bottom roller pairs. A slide member 28 can enter a suitable hole 29 in an associated strut 26 when the opposed pair of belt drives is closed towards each other. The carriage also supports upper and lower opposed pairs of rollers 36 which are captured by outer tracks (not shown) on a housing 38 (FIG. 4) which is secured to the machine frame to depend over the inspection area.

When an open/close step motor 40 is operated (there is a motor for each opposed pair of belt drives), a pulley drives a screw 44 which is threadedly received by a corresponding nut secured within the lower slide member (not shown in FIG. 4) which displaces the lower slide member and the attached strut. Operation of an open/close motor will accordingly conjointly horizontally displace the upper belt/lower belt drives either towards or away from each other.

The housing 38 is integral with a mounting 39 which is secured to the machine frame and mounted on the housing are a pair of up/down motors 50. One motor is associated with the upper drive belts and the other is associated with the lower drive belts. Each motor operates a pulley 42 which rotatably drives a screw which is operatively received by an elongated nut 52 which is joined to the carriage via a bracket 54.

Figure 5:
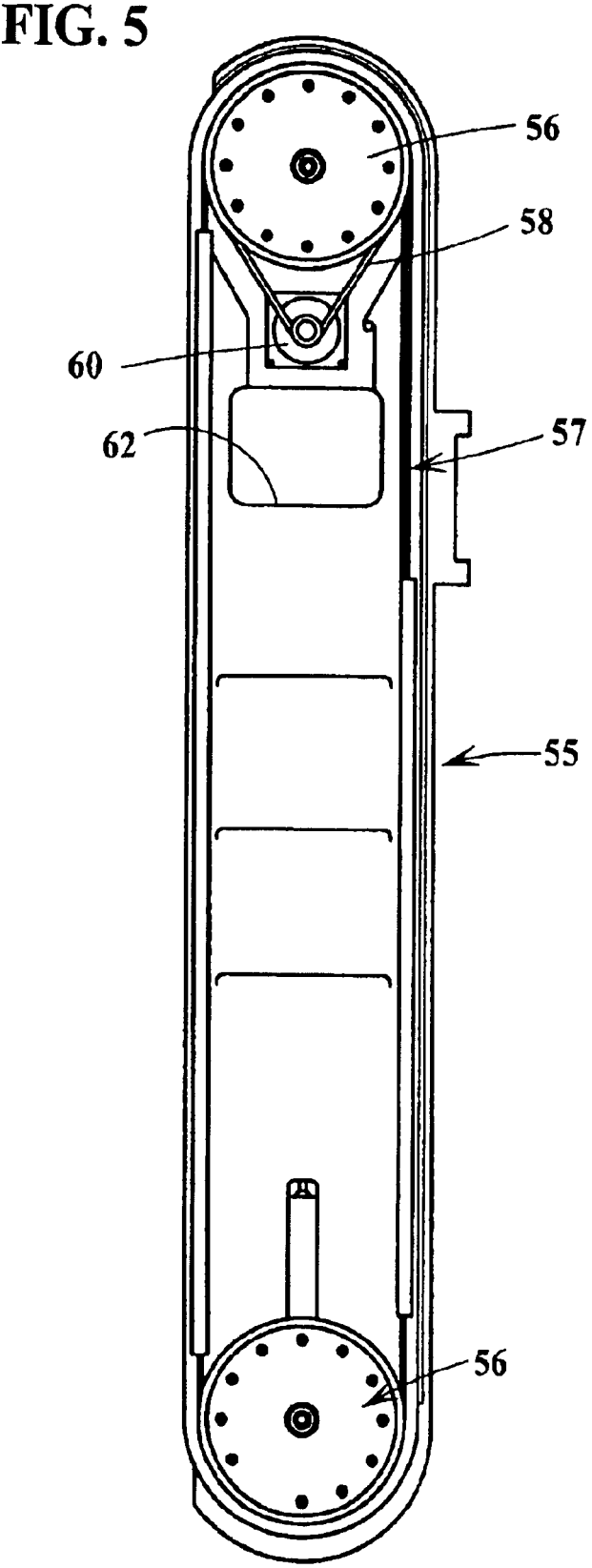
FIG. 5 is a bottom view of a belt drive unit.

Each belt drive (FIG. 5) has a housing or arm 55 which supports a pulley 56 at either end of the arm. These pulleys, which support a belt 57, is driven via a timing belt 58 interconnecting one of these pulleys with a step motor drive 60. The step motor is mounted on top of the casing as shown in FIG. 2. The step motor for a lower belt drive is mounted on the top surface of the lower casing so that it can enter a pocket or cutout 62 defined in the upper casing. To facilitate vertical displacement, each assembly is counterbalanced to substantially remove the weight of the assembly.

FIG. 2 shows the upper and lower belt drive pairs being located in a large ware 12A configuration with the upper and lower belt drives being vertically stacked.

Figure 6:
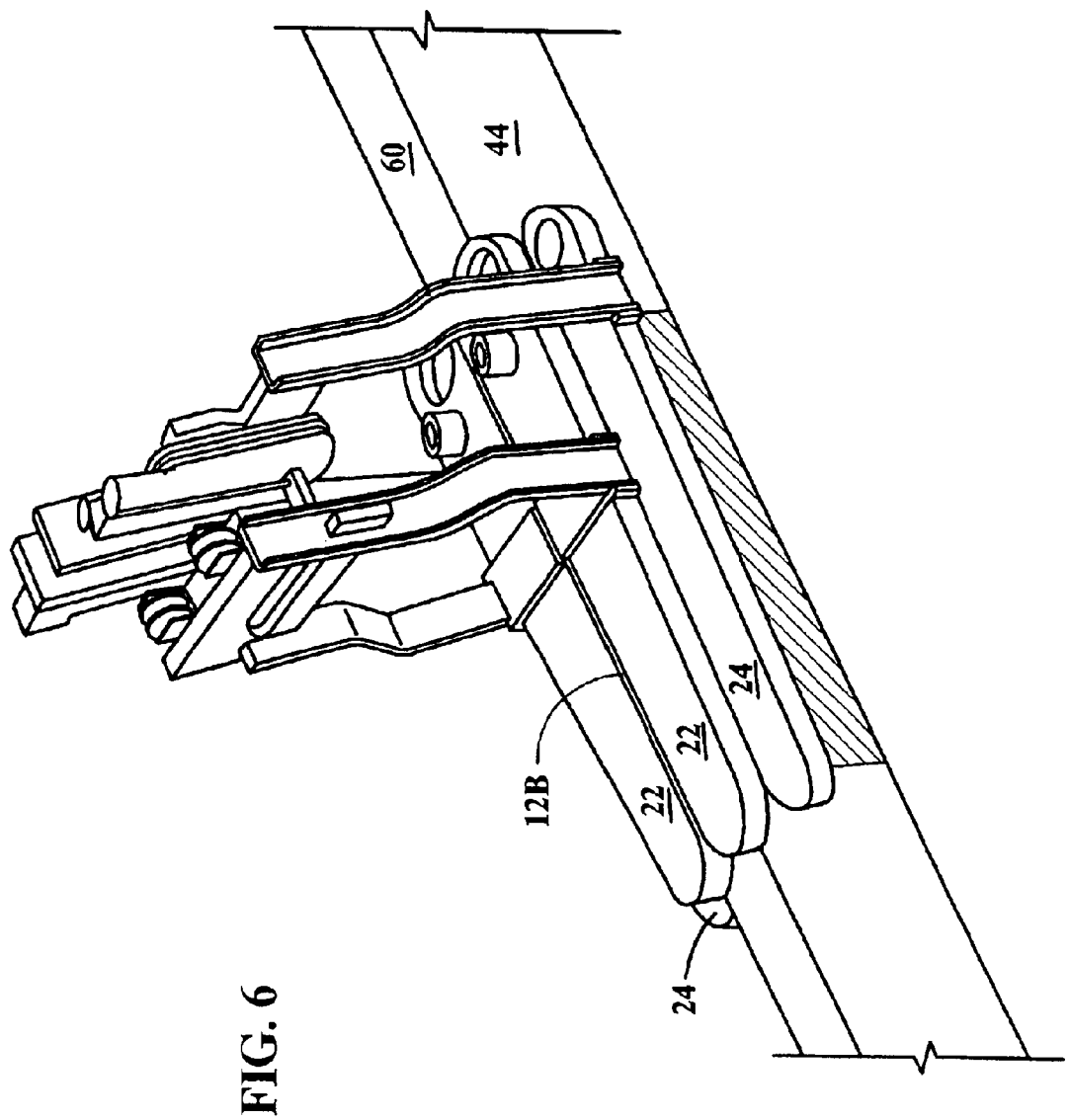
FIG. 6 is an oblique view of the belt drive assembly of the machine illustrated in FIG. 1 in the mini ware configuration.

FIG. 6 illustrates the location of the upper and lower drive belt pairs in a small or mini ware 12B configuration. To reach this configuration the upper belt drive pair is elevated to separate the vertically adjacent belt drives so that they can be displaced relatively horizontally (the top of the motor on the lower drive is clear of the upper casing). The lower belt drive pair is horizontally separated to the location where both lower belt drives are horizontally cleared of the front wall 17,18 of the conveyor. The lower belt drives are then lowered until the top of the belt drive (its motor) is below the surface 60 of the infeed/outfeed conveyors. Finally, the upper drive belt pair is now lowered to a location where the casing is just above the top surface 60 of the conveyor. Now the drive belts of the upper drive belt pair can be located adjacent the sidewall of mini ware 12B.

What is claimed is:

1. A belt drive conveyor system for a machine for inspecting containers comprising a belt drive conveyor mechanism for picking up a bottle at a pick up location and delivering the picked up bottle to a release position, said belt conveyor mechanism comprising upper and lower opposed pairs of belt drives means for supporting the upper and lower opposed pairs of belt drives so that 1. the upper drive belt pair can be raised to a vertical location whereat there can be relative horizontal movement between the upper and lower drive belt pairs;

2. the lower drive belt pair can be separated and lowered to an out of the way location; and
   3. the upper drive belt pair can then be lowered to be the only belt pair engaging a small container.

2. A belt drive conveyor system for a machine for inspecting containers according to claim 1, wherein each belt drive includes a belt drive casing, belt supporting means mounted on said belt drive casing, said belt supporting means having a drivable member, and motor means mounted on said casing for driving said drivable member.

3. A belt drive conveyor system for a machine for inspecting containers according to claim 2, wherein said means for supporting the upper and lower opposed pairs of belt drives comprises first support means for supporting the upper opposed pair of belt drives cantilevered towards each other so that the belts of the opposed pair of belt drives can engage and drive a container, second support means for supporting the lower opposed pair of belt drives cantilevered towards each other so that the belts of the opposed pair of belt drives can engage and drive a container, said first and second support means each including a vertical bracket secured to each belt drive, horizontal displacement means including a motor for conjointly displacing said vertical brackets towards or away from each other to open or close said belt drives, and vertical displacement means including a motor for raising or lowering said horizontal displacement means.

* * * * *